US010602925B2

(12) United States Patent
Sarunic et al.

(10) Patent No.: US 10,602,925 B2
(45) Date of Patent: Mar. 31, 2020

(54) COHERENCE-GATED WAVEFRONT-SENSORLESS ADAPTIVE-OPTICS MULTI-PHOTON MICROSCOPY, AND ASSOCIATED SYSTEMS AND METHODS

(71) Applicant: Simon Fraser University, Burnaby (CA)

(72) Inventors: Marinko Sarunic, Burnaby (CA); Yifan Jian, Burnaby (CA); Eunice Michelle Cua, Burnaby (CA); Stefano Bonora, Padua (IT); Robert J. Zawadzki, Sacramento, CA (US)

(73) Assignee: Simon Fraser University, Burnaby (CA)

( * ) Notice: Subject to any disclaimer, the term of this patent is extended or adjusted under 35 U.S.C. 154(b) by 0 days.

(21) Appl. No.: 15/758,973

(22) PCT Filed: Sep. 12, 2016

(86) PCT No.: PCT/US2016/051369
§ 371 (c)(1),
(2) Date: Mar. 9, 2018

(87) PCT Pub. No.: WO2017/044969
PCT Pub. Date: Mar. 16, 2017

(65) Prior Publication Data
US 2018/0242838 A1 Aug. 30, 2018

Related U.S. Application Data

(60) Provisional application No. 62/217,508, filed on Sep. 11, 2015.

(51) Int. Cl.
*A61B 3/10* (2006.01)
*G01B 9/02* (2006.01)
(Continued)

(52) U.S. Cl.
CPC ............ *A61B 3/102* (2013.01); *A61B 3/0025* (2013.01); *A61B 3/1225* (2013.01); *A61B 3/14* (2013.01);
(Continued)

(58) Field of Classification Search
CPC ......... A61B 3/102; A61B 3/14; A61B 3/1225; A61B 3/0025; G01B 9/02038;
(Continued)

(56) References Cited

U.S. PATENT DOCUMENTS

2006/0061769 A1 3/2006 Yang et al.
2013/0100405 A1 4/2013 Porter et al.
(Continued)

OTHER PUBLICATIONS

International Search Report dated Dec. 5, 2016 in International Application No. PCT/US2016/051369, filed Sep. 12, 2016, 3 pages.
(Continued)

*Primary Examiner* — Tuyen Tra
(74) *Attorney, Agent, or Firm* — Christensen O'Connor Johnson Kindness PLLC

(57) ABSTRACT

In one embodiment, a sensorless adaptive optics imaging system includes a source of light, an optical delivery unit having a wavefront modifying element, and an optical coherence tomography (OCT) sensor configured to acquire OCT images based on light emitted by the source of light and transmitted through the optical delivery unit. The system also includes a processing unit that can: process the OCT images, and determine an adjustment of parameters of the wavefront modifying element. In some embodiments, the system includes a multi-photon microscopy (MPM) sensor that acquires MPM images based on the light transmitted through the optical delivery unit.

19 Claims, 10 Drawing Sheets

(51) Int. Cl.
*G02B 21/00* (2006.01)
*A61B 3/00* (2006.01)
*A61B 3/12* (2006.01)
*A61B 3/14* (2006.01)

(52) U.S. Cl.
CPC ..... *G01B 9/02029* (2013.01); *G01B 9/02038* (2013.01); *G01B 9/02044* (2013.01); *G01B 9/02067* (2013.01); *G01B 9/02091* (2013.01); *G02B 21/0028* (2013.01); *G02B 21/0076* (2013.01)

(58) Field of Classification Search
CPC ............ G01B 9/02067; G01B 9/02091; G01B 9/02044; G01B 9/02029; G02B 21/0076; G02B 21/0028
USPC .......................................... 351/200, 205, 206
See application file for complete search history.

(56) References Cited

U.S. PATENT DOCUMENTS

2014/0104618 A1  4/2014  Potsaid et al.
2014/0328365 A1  11/2014  Grujic et al.

OTHER PUBLICATIONS

Written Opinion of the International Searching Authority dated Dec. 5, 2016 in International Application No. PCT/US2016/051369, filed Sep. 12, 2016, 9 pages.

Bonora, et al. "Wavefront Correction and High-Resolution In Vivo OCT Imaging With an Objective Integrated Multi-Actuator Adaptive Lens," Optics Express, vol. 23, No. 17, pp. 21931-21941, Aug. 13, 2015.

Graf, et al. "Multimodal In Vivo Skin Imaging With Integrated Optical Coherence and Multiphoton Microscopy," IEEE Journal of Selected Topics in Quantum Electronics, 18(4): 1280-1286, Jun. 27, 2012.

Ji, et al. "Adaptive Optics Via Pupil Segmentation for High-Resolution Imaging in Biological Tissues," Nature Methods, 7, 141-147, Dec. 27, 2009.

Wang, et al. "Optimum Deformable Mirror Modes for Sensorless Adaptive Optics," Optics Communications, 282 (2009), pp. 4467-4474.

Wong, et al. "In Vivo Imaging of Human Photoreceptor Mosaic with Wavefront Sensorless Adaptive Optics Optical Coherence Tomography," Biomedical Optics Express, Feb. 1, 2015.

Jian Yifan et al., "Wavefront sensorless adaptive optics optical coherence tomography for in vivo retinal imaging in mice," Biomedical Optics Express, vol. 5, No. 2, Feb. 1, 2014, 13 pages.

Graf, Benedikt et al., "Multimodal In Vivo Skin Imaging with Integrated Optical Coherence and Multiphoton Microscopy," IEEE Journal of Selected Topics in Quantum Electronics, IEEE Service Center, Piscataway, NJ, vol. 18, No. 14, Jul. 1, 2002, pp. 1280-1286.

European Search Report dated Jan. 31, 2019, issued in corresponding European Application No. 16845288.6, filed Sep. 12, 2016, 9 pages.

International Preliminary Report on Patentability dated Mar. 13, 2018 in International Application No. PCT/US2016/051369, filed Sep. 12, 2016, 10 pages.

COHERENCE-GATED WAVEFRONT-SENSORLESS ADAPTIVE-OPTICS MULTI-PHOTON MICROSCOPY, AND ASSOCIATED SYSTEMS AND METHODS

CROSS-REFERENCE(S) TO RELATED APPLICATION(S)

This application claims priority to U.S. Application No. 62/217,508, filed Sep. 11, 2015, expressly incorporated herein by reference in its entirety.

FIELD OF THE INVENTION

The present invention relates generally to image acquisition and processing, and more particularly relates to methods and apparatus for image-based diagnostics of the eye.

BACKGROUND

Multi-photon microscopy (MPM) is an imaging technology that is used to obtain 3-D images from biological specimens with molecule specific contrast. The use of MPM for in vivo microscopy has multiple potential benefits over single photon microscopy, including applications such as non-invasive diagnostic imaging of the retina (the light sensitive tissue at the back of the eye). Compared to conventional microscopy with single photon excitation fluorescence, MPM uses light at longer wavelengths, in the near infrared (NIR), where tissue scattering and absorption is lower. The use of NIR light is particularly attractive for imaging the retina, which contains phototransduction pigments sensitive to the visible wavelengths. Unlike single photon processes, MPM techniques, such as two-photon excited fluorescence (TPEF), only occur at a narrow axial range around the focal point where the irradiance is the highest, providing an optical sectioning effect. However, a disadvantage of MPM imaging in ocular tissues is the high pulse energy required to elicit the non-linear effects. Minimizing the incident exposure energy is therefore important for non-invasive imaging, in particular for the delicate tissues of the retina.

Although MPM is relatively unaffected by low levels of out-of-focus scattering, wavefront aberrations from the sample and optical path cause blurring of the focal spot. Since the MPM signal is quadratically proportional to the focused spot size, significant improvements in the signal-to-noise ratio can be achieved through wavefront shaping to approach the diffraction-limited focus with a large numerical aperture.

Some conventional technologies apply adaptive optics (AO) to MPM to correct for refractive errors and promote diffraction-limited focusing in tissue. These conventional AO systems use a Hartmann-Shack Wavefront Sensor (HS-WFS) to detect the wavefront aberrations and, in a closed feedback loop control, guide the shape of an adaptive element, such as a deformable mirror, to correct the detected wavefront aberrations. Since the HS-WFS is sensitive to back-reflections, the conventional AO systems use curved mirrors instead of lenses, and long focal lengths to minimize the off-axis aberrations. Furthermore, the use of a wavefront sensor places significant design constraints on the system, requiring optical conjugation of the deformable element, WFS, and the pupil plane of the system. Additionally, the HS-WFS is generally only useful when there is a single scattering plane in the sample, because thick tissue samples or multi-layered samples negatively affect the ability to measure the wavefront.

Furthermore, conventional MPM techniques may require relatively long time, e.g., 6-7 minutes for image acquisition using high power laser excitation energy. Therefore, these conventional technologies subject the patient's eye to a relatively long period of high stress.

Accordingly, there remains a need for the eye imaging methods, systems and apparatuses that are relatively fast and do not cause high light-induced stress on the retina.

DESCRIPTION OF THE DRAWINGS

The foregoing aspects and the attendant advantages of this invention will become more readily appreciated as the same become better understood by reference to the following detailed description, when taken in conjunction with the accompanying drawings, wherein.

DETAILED DESCRIPTION

Specific details of several embodiments of representative image acquisition and processing system, and associated methods are described below. The system and methods can be used for the imaging and diagnostics of the eye. A person skilled in the relevant art will also understand that the technology may have additional embodiments, and that the technology may be practiced without several of the details of the embodiments described below with reference to FIGS. 1-8G.

In order to be effective, the combination of adaptive optics (AO) with multi-photon microscopy (MPM) for retinal imaging should be fast (on the order of seconds), and should minimize the high-energy laser exposure on the retina. A person of ordinary skill would know that adaptive optics or wavefront modifying elements (e.g., adaptive lenses, adaptive mirrors, adaptive liquid crystals) can act on light to modify the phase front, aberrations, etc. in order to change/adjust the optical properties of an optical system, such as the focal length, size and distortions of the focal point, etc. In some embodiments of the inventive technology, MPM imaging is combined with depth-resolved wavefront sensorless AO (WSAO) using the same light source, but separate detection systems. The WSAO typically can change its own optical properties without having to rely on the optical sensors that are part-of or are associated-with to the AO itself. The light used for MPM microscopy typically comprises of a train of pulses that are on the order of femtoseconds in duration. The femtosecond-pulsed laser can be selected to have adequate bandwidth (tens of nanometers) for optical coherence tomography (OCT) with coherence length on the order of microns. Coherent detection of the excitation light that is back-scattered from the sample enables OCT-like cross-sectional visualization of the sample. In at least some embodiments, due to the high sensitivity of OCT detection, a cross-sectional profile of the sample can be visualized that is much larger than the Rayleigh range of the focused beam.

The OCT images can be used for image-guided WSAO aberration correction of the excitation beam in the sample. The OCT images can be acquired at low power since the back-scattered light used for the OCT detection is a single photon process. Following the aberration correction, the intensity of the excitation laser can be increased to perform the MPM imaging, which is acquired using a dedicated highly sensitive detector. Both the MPM and the OCT image acquisition sub-systems can share the same source and optical delivery unit delivery optics (including the WSAO) to ensure exact co-registration of the images during acquisition.

Figure 1:
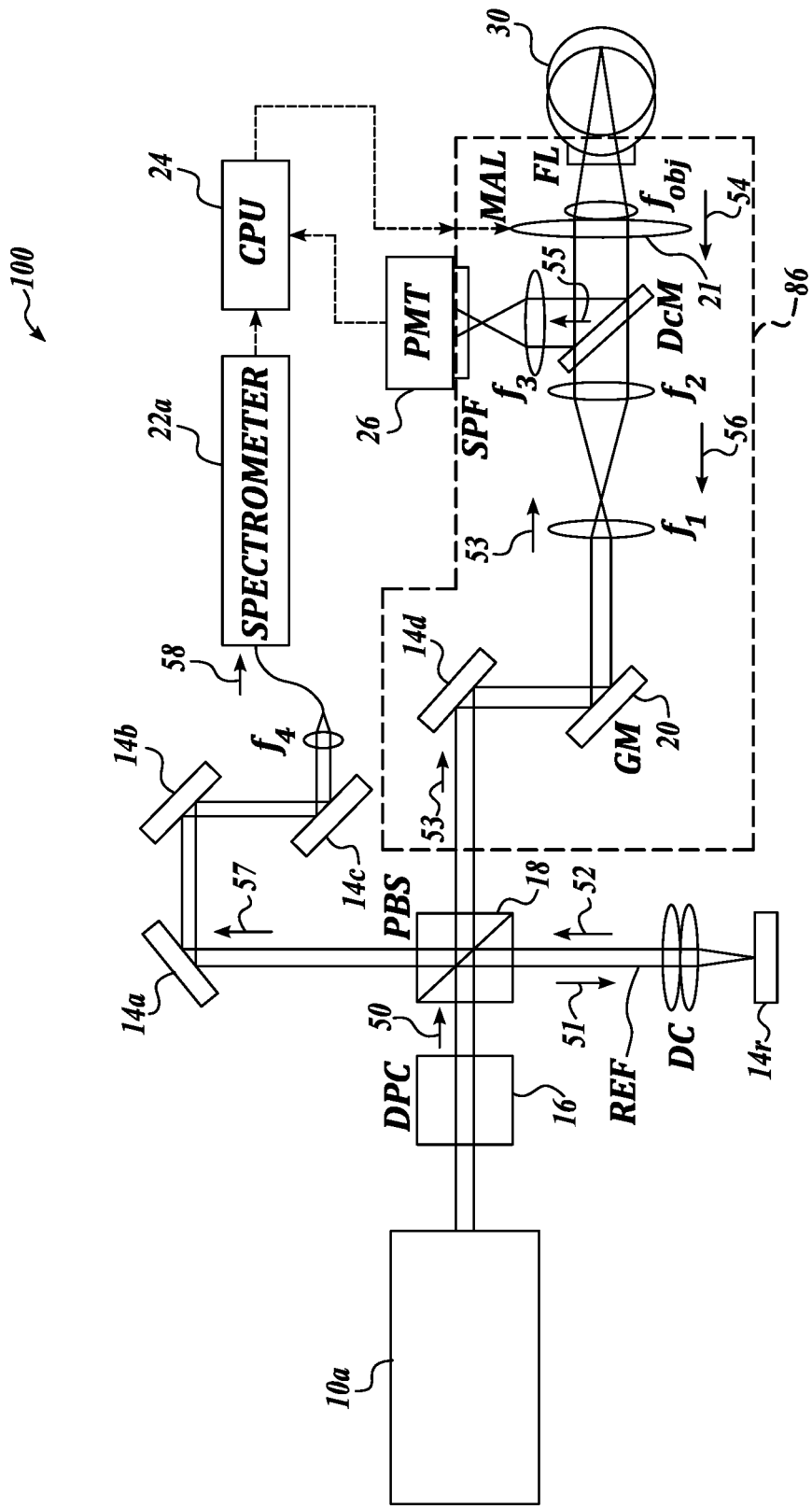
FIGS. 1-3 are schematic views of image acquisition systems in accordance with embodiments of the presently disclosed technology.

FIG. 1 is a schematic view of an image acquisition system 100 in accordance with embodiments of the presently disclosed technology. Briefly stated, FIG. 1 shows a spectral domain OCT system comprising a light source 10a in the source arm, a mirror 14r in a reference arm REF, optical delivery unit directing light on a sample 30 in a optical delivery unit 86, a spectrometer (i.e., an OCT sensor or detector) 22a in detection arm, and a beam splitter 18. The beam splitter splits the source-light into the reference arm and optical delivery unit. The reference mirror is typically installed on a translation stage so that it can be moved back and forth to increase or decrease the path-length in the reference arm. The light-beams returning from the reference mirror and the sample return to the beam-splitter, and are further split into the source and detector arms. The light source can be a broad-band light source. For example, the full-width-half-max (FWHM) spectral width of the light source may range from 10 nm to 150 nm.

Spectral domain OCT systems use spectroscopic detection method for measuring the interference generated from the light returned from the sample and reference arms. Generally, the interferometric light exiting the detector arm is dispersed via a grating. The spectra are acquired using a line-scan camera. The resulting spectra can be transferred to a processor for inverse Fourier transforming and relevant signal processing (such as obtaining the complex envelope of the interferometric signal) for obtaining depth dependent (i.e., axial) reflectivity profiles (A-scans). The axial resolution is governed by the source coherence length, typically about 3-10 µm. Two dimensional tomographic images (B-scans) are created from a sequence of axial reflectance profiles acquired while scanning the probe beam laterally across the specimen or biological tissue. Details of the system illustrated in FIG. 1 are described below.

The source light 10a can include a laser (e.g., a 1560 nm femtosecond laser by Menlo Systems, Germany). In some embodiments, the laser can have a 120 nm (or other) bandwidth and 47 fs (or other) pulse duration at the laser output. The source of light 10a can also include a second-harmonic-generating (SHG) module (not shown) to frequency-double the light source from, e.g., 1560 nm to 780 nm. The wavelength of 780 nm can be used as the MPM excitation source as well as OCT light source, as explained in more detail below. In the illustrated embodiment, the 780 nm light was directed through a dispersion-pre-compression (DPC) 16 to compensate for the group delay dispersion from the optical elements and to provide approximately transform-limited pulse duration at the sample in order to maximize the MPM signal (generally, shorter pulses provide a larger MPM signal). In some embodiments, the dispersion pre-compression can be adjustable to accommodate different samples, for example a mouse eye. After pulse dispersion pre-compensation, the light can be split by the pellicle beam splitter (PBS) 18. In some embodiments, 95% (or other fraction) of the power in a beam 50 can be directed towards the sample through the optical delivery unit as a beam 53, and 5% (or other fraction) of the power towards a reference arm REF as a beam 51, which reflects back toward the PBS 18 as a beam 52, and further to mirrors 14a-14c as a beam 57. The terms "beam" and "light" are used interchangeably in this application to denote electromagnetic radiation either in a visible or in an invisible (e.g., infrared) spectrum.

In some embodiments, the optical delivery unit 86 can one or more scanning mirrors 20, e.g., galvanometer-scanning mirrors (GM) or MEMS scanning mirrors, to scan the light across the surface of the sample within an eye 30. Two lenses $f_1$ and $f_2$, having the focal lengths of, e.g., 60 mm and 200 mm, respectively, can relay the conjugate plane from the GM to the objective lens $f_{obj}$ having a focal length of, e.g., 8 mm. A mirror 14d also directs the light coming from the scanning mirrors 20 to the PBS 18. A wavefront modifier such as an adaptive optics (AO) lens or a deformable mirror 21, e.g., a Multi-actuator Adaptive Lens (MAL), can be placed adjacent to the objective lens $f_{obj}$. A person of ordinary skill would know other suitable types of wavefront modifiers or adaptive elements or adaptive optics elements or adaptive optics, e.g., a liquid crystal spatial light modulator, deformable mirror, or any other spatial light modulator, e.g. digital micromirror display, affecting the phase and/or intensity, can be used to modify the wavefront for aberration corrections and wavefront optimization. In at least some embodiments, a transmissive deformable component or wavefront modifier (e.g., an adaptive optics 21 that is a lens) enables a compact optical configuration, which may be important when using the technology in the vision science laboratories or clinical settings. A benefit of using transmissive elements for adaptive optics is that the wavefront modifying (or correcting) element can be placed adjacent to a pre-defined pupil plane without the need for an extra optical relay, thus further reducing the footprint of the optical system 100.

A back-scattered excitation light 54 can be transmitted back as the light 56 by a dichroic mirror DcM and gets de-scanned at the scanning mirror 20. The de-scanned beam is recombined with the reference arm light 52 at the beam splitter 18, and directed to a spectrometer 22a (also referred to as an OCT sensor) as the light 57, 58. The sample light 56 and reference light 52 can generate an interference pattern on the spectrometer detector 22a. In some embodiments, the interference pattern can be processed into cross-sectional images using a graphical processing unit (GPU) 24 with associated software. In some embodiments, a central processing unit (CPU) or a GPU/CPU combination can be used with associated software. In some other embodiments, an embedded processor or Field Programmable Gate Array (FPGA) processor or an application specific integrated circuit (ASIC) with associated software can be used.

A back-scattered excitation light 54 includes a two-photon excited fluorescence emission from the sample 30 that gets reflected as light 55 by the dichroic mirror DcM to a MPM sensor or detector such as a photo-multiplier tube (PMT) 26 without being de-scanned by the scanning mirror 20. In some embodiments, the two-photon excited fluorescence (or multi-photon signal) may be de-scanned by the scanning mirrors. One can use any other photodetector instead of the PMT as a MPM sensor. In some embodiments, a short-pass filter SPF and a focusing lens $f_3$ are placed prior to the PMT (i.e., MPM sensor) to reject residual excitation light. In many embodiments, the back-scattered excitation light 54 includes both the excitation light and the two-photon excited fluorescence light. The excited light could include multi-photon light such as second or third harmonic generation light, etc. Furthermore, the excitation light may carry many times more energy than the two-photon excited fluorescence light. Therefore, the SPF can be used to let only the two-photon excited fluorescence light or multi-photon light into the PMT detector (i.e., the MPM sensor).

In some embodiments, acquisition of the OCT A-scans is synchronized to the acquisition of the MPM sensor, which ensured that both OCT and MPM images are properly registered.

The optical system described using dual wavefront modifying elements for light delivery to the human eye could be readily adapted for MPM imaging with aberration correction using the OCT images for WSAO. The importance of aberration correction is emphasized in order to maintain the smallest possible focal spot on the retina (diffraction limited with full pupil illumination) in order to minimize the optical energy required to generate the MPM signal from the retina. In order to excite non-linear processes, a short duration pulsed light source would be preferred. A highly sensitive MPM sensor such as a photomultiplier tube would be placed between the final lens and the subject's eye, using a dichroic mirror to reflect the two-photon excited fluorescence (TPEF) from the eye but passing the excitation beam. The laser power could be reduced during the aberration correction steps. Alternatively, since criteria for maintaining the minimum power exposure levels for humans is even more important than that for preclinical imaging, a second low power continuous wave (CW) broadband light source at the same wavelength could be co-aligned with the femtosecond laser input; the low power source could be used for optimization with the femtosecond laser off, and then after aberration correction is achieved, the low power laser can be turned OFF and the femtosecond laser turned ON for MPM imaging.

Figure 2:
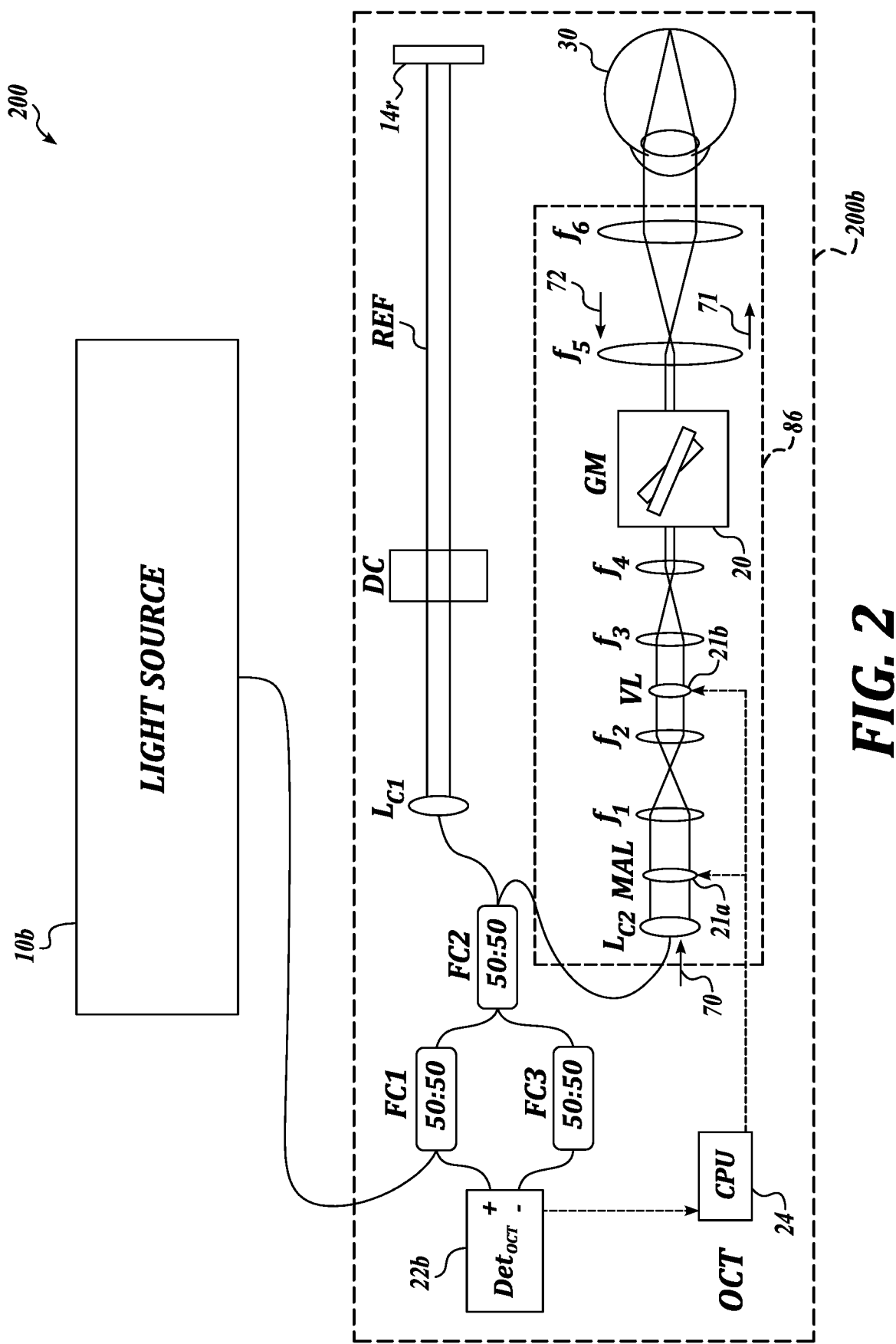

FIG. 2 is a schematic view of the image acquisition system 200 in accordance with an embodiment of the presently disclosed technology. Briefly stated, in the OCT system 200, the broad-band light source (e.g., the light source 10a in FIG. 1) is replaced by a tunable frequency light source 10b. The detector array (e.g., the spectrometer 22a in FIG. 1) is replaced by a single detector 22b (or dual detectors for balanced detection). In some embodiments, the grating may not be needed in the system of FIG. 2. The wavelength of the source 10b can be tuned relatively rapidly (e.g., at a rate of 10 kHz-1 MHz) within a spectral range of typically 10 nm to 100 nm around the center wavelength. The instantaneous line width (spectral range of the tunable filter) is commonly better than 0.1 nm. In some embodiments, the average power of such a source generally ranges from 0.1 mW to 40 mW depending upon the applications. The source 10b may be electrically operated. Analog to digital converter (ADC) can be added to digitize the detector current for subsequent digital processing. Details of the system illustrated in FIG. 2 are described below.

The detector 22b (also referred to as an OCT detector or a high speed detector or an OCT sensor) can be a photo-diode that converts light into electricity. The OCT sensor or detector may be a high-speed detector with the bandwidth of up to few hundred MHz. The OCT sensor or detector may be coupled with a high-speed A/D (analog to digital) converter, e.g., 8-bit or 12-bit converter, with a conversion rate of 0.1-2 GSamples/second. The relatively high conversion rate assists in achieving typical line-rates (rate of acquisition of A-scans) of 10,000 lines/s to 1 million lines/s.

The light source 10b for imaging the retina in the eye 30 can be a wavelength-swept laser (e.g., a wavelength-swept laser by Axsun Inc. with an 80 nm full-width half-maximum (FWHM) spectrum centered at 1060 nm). In general, the wavelength of the light produced by the wavelength-swept laser is in a narrow band, but is also a function of time, i.e., the wavelength sweeps in a given period of time. In some embodiments, the line rate of the light source can be 100 kHz, with approximately 50% duty cycle. In order to increase the imaging speed, a 'double buffered' approach can be implemented in some embodiments in conjunction with a Fiber Bragg Grating (FBG) to align A-scans in real time.

The OCT system 200 includes the optical delivery unit 86 and the reference path REF. The optical delivery path 86b can include wavefront modifying elements 21a and 21b (e.g., deformable lenses MAL and VL), relay lenses $f_1$-$f_6$, and the scanning mirrors 20 (e.g., galvanometer mounted mirrors GM) to deliver a scanning beam 71 to the pupil of the eye of the subject being imaged (e.g., to the eye 30). The wavefront modifying element 21a can be placed at the location of a collimating lens $L_{C2}$, which collimates a light 70 from the fiber. This optical plane is conjugated to the adaptive optics element or wavefront modifier 21b (e.g., a deformable variable focus lens VL by ARCTIC 316-AR850, Lyon, France) via an optical relay. In some embodiments, the dual wavefront modifying elements 21a and 21b can create a 'woofer-tweeter' adaptive optics system. For example, the wavefront modifying element 21b (VL or "woofer") can correct low order aberrations, while the wavefront modifying element 21a can correct higher order aberrations (MAL or "tweeter"). Two additional relays are used to conjugate the optical plane to the scanning mirrors 20 (e.g., an XY galvanometer mounted mirror GM, or MEMS scanning mirrors or other ways of scanning the beams), and then to the subject's eye's pupil. In some embodiments, the $1/e^2$ beam diameter at the pupil is approximately 5 mm. A returning light 72 propagates back through the optical elements, and can be acquired by an OCT sensor or detector 22b, together with a reference beam from a reference path REF. In some embodiments, the fiber optics couplers FC1 and FC2 can be replaced by fiber-optic circulators.

In some embodiments, the wavefront modifying element 21b (e.g., the variable focus lens) can accommodate for the variation in subject's eyes up to approximately −6 diopters without mechanically moving lenses or the pupil plane. In some embodiments, due to the non-linearity and comparatively slow response time of the variable focus lens 21b, the focus can be adjusted manually to the retinal layer of interest using the cross-sectional OCT images as guidance. The position of the focus within the retina is readily observed as the brightness of the layers changed dynamically as the shape of the lens is changed.

In some embodiments, the lenses can be standard achromatic doublets by Thorlabs Inc. and Edmund Optics, Inc. The total length of the optical delivery unit can be 1.5 m, and can be folded to fit on an optical breadboard mounted to a slit lamp base, therefore providing three dimensional translation of the imaging system relative to the subject's eye. The optical delivery unit can also be mechanically designed and assembled to have a chin-rest and 3-dimensional degrees of freedom. In some embodiments, the field of view limited by the diameter of the last optical relay is 4°×4°. The field of view can be expanded or shrunk as desired using appropriate lenses.

If used for multi-photon microscopy (MPM), the OCT engine could be modified with a pulsed femtosecond laser and a spectrometer based OCT sensor/detection system, as shown with reference to FIG. 1. In the embodiments illustrated in FIG. 2 and FIG. 1, the OCT data can be processed and displayed in real time using a Graphics Processing Unit (GPU) platform and/or a CPU platform. In some embodiments, the GPU processing can be integrated with controls for the wavefront modifiers, merit function calculation, and real-time axial tracking of the retinal position in software.

In the above implementations of OCT, Fourier Domain (FD) is often used interchangeably with Spectrometer Based (SD) OCT. Furthermore, FD is sometimes used to describe both SD and Wavelength Tunable Swept Source (SS) OCT. Another term of art for the SS OCT is Optical Frequency Domain Imaging (OFDI). In some embodiments, these techniques may be complementary to the Time Domain (TD) OCT described below.

In time-domain OCT, the light source is typically a broad-band source. The axial (or depth) ranging can be achieved by continuously moving the reference mirror back and forth (typically using a motorized translation stage) while simultaneously monitoring the interferometric signal using an OCT sensor such as a single detector (or dual detectors for balanced detection). The interferometric signal is demodulated (either outside or inside the processor) to generate A-scans. Two dimensional tomographic images (B-scans) are created from a sequence of axial reflectance profiles acquired while scanning the probe beam laterally across the specimen or biological tissue. Therefore, in some embodiments, the OCT systems in FIGS. 1-3 may be replaceable with the time-domain OCT by, for example, making the reference mirror moveable and using an OCT sensor such as a single detector (or dual balanced detectors) like in FIG. 2 or replacing the spectrometer in FIGS. 1 and 3. The light source can be a broad-band source. Thus, the reference arm has a reference mirror and the reference mirror location is adjusted for coherence gating and generating OCT A-scans as well as B-scans and 3-D volumes.

Figure 3:
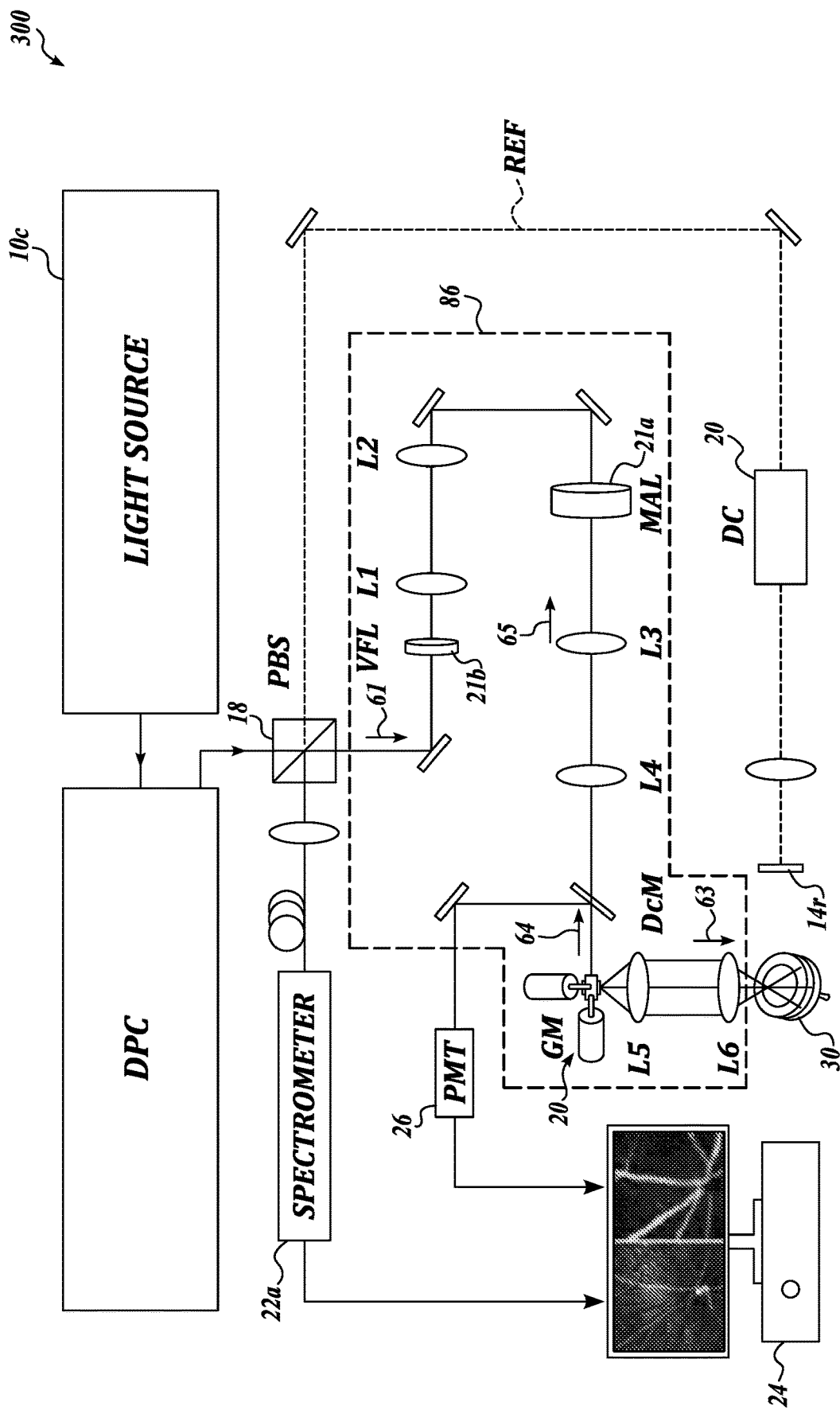

FIG. 3 is a schematic view of the image acquisition system 300 in accordance with an embodiment of the presently disclosed technology. The illustrated embodiment is generally similar to the one shown in FIG. 2. The system 300 includes two wavefront modifying elements 21a and 21b in the path of light emitted by a light source 10c. In some embodiments, the wavefront modifying elements 21a and 21b can operate as a "tweeter-woofer" pair. For example, the wavefront modifying element 21b (VFL or "woofer") can correct low order aberrations, while the wavefront modifying element 21a can correct high order aberrations (MAL or "tweeter"). In the illustrated embodiment, the adaptive optics (or wavefront modifying) element 21a (MAL) was used for fine tuning of the focus as well as higher order aberration correction. In some embodiments, the corrected modes can be defocus, two astigmatisms, two coma, sphere, and two trefoils, corresponding to Zernike modes 4, 3, 5, 7, 8, 12, 6, 9, respectively. Higher modes can also be corrected without limitation. We are mentioning Zernike modes, but the proposed invention is applicable to other ways of describing wavefronts as well. For example, an alternative to Zernike modes can be another orthogonal-basis set, e.g., Lukosz polynomials. In some other embodiments, a non-orthogonal basis can also be used. Every wavefront modifying element has its own natural modes. These modes can be orthogonal, but it is not strictly necessary. Sometimes these modes may not be orthogonal. The modes can be a linear combination of the actuator functions that influence the wavefront and the adaptive or wavefront modifying element. Sometimes it might be more convenient for the wavefront modifier to operate using these modes. In some embodiments, the relative positions of the "woofer" and "tweeter" may be interchanged with respect to their illustrated positions.

Figure 4:
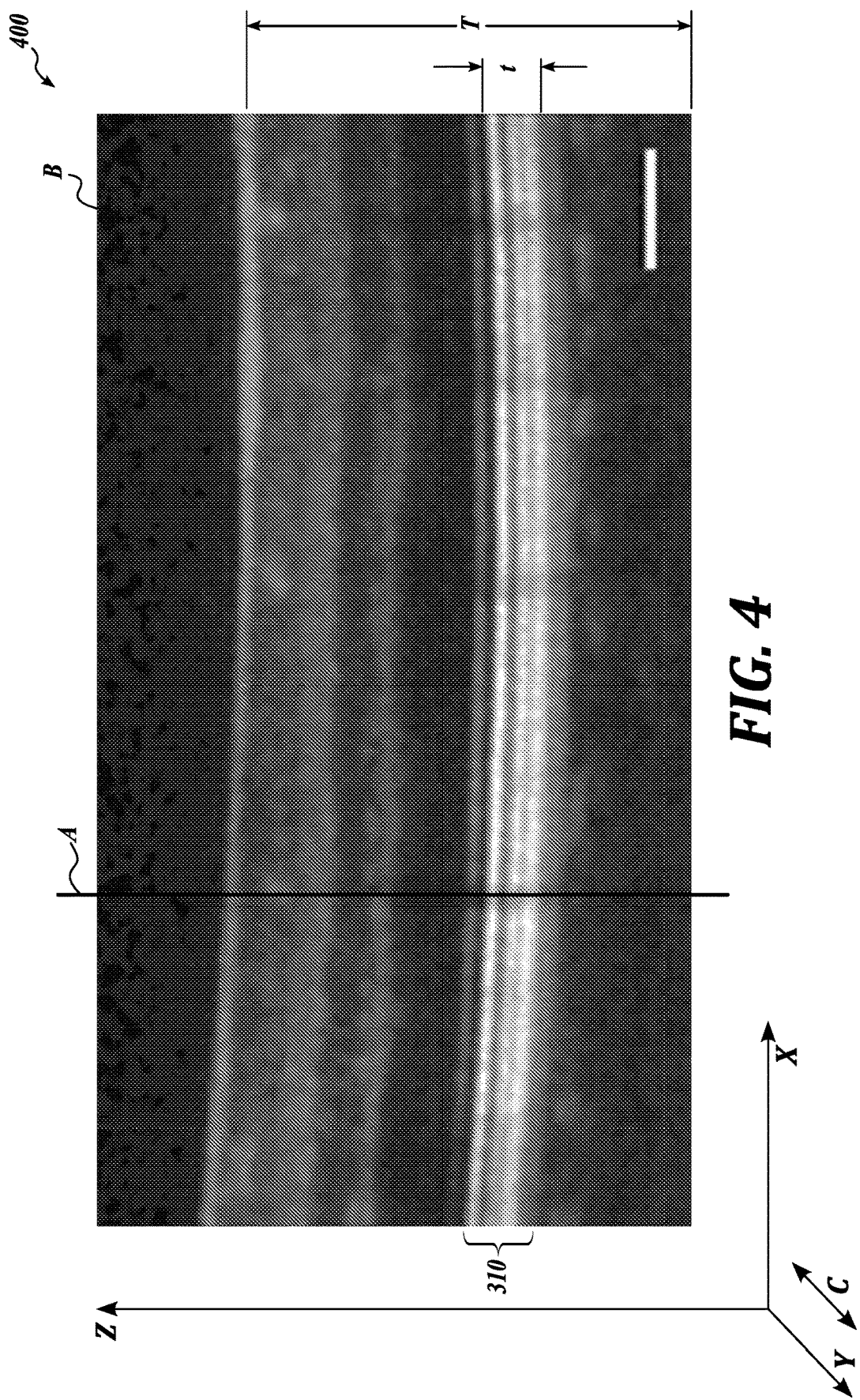
FIG. 4 is a sample cross-sectional view of the eye acquired in accordance with an embodiment of the presently disclosed technology.

FIG. 4 is a sample cross-sectional view 400 of the human eye acquired in accordance with an embodiment of the presently disclosed technology. Five research volunteers were imaged. The maximum power at the cornea was 750 µw. Retinal imaging was performed without mydriasis. Since the wavelength was outside the visible spectrum, the imaging beam did not cause constriction of the pupil, and subjects with a pupil larger than 5 mm could be readily imaged. Imaging was performed with the subjects seated at a table with forehead and chin rest; a bite bar was not used during imaging. The operator aligned the imaging beam to the subject's eye under the guidance of a pupil camera that permitted the position of the infrared beam to be observed.

The cross-sectional view includes multiple A-scans in the direction that is generally perpendicular to the retina (Z-direction). In some embodiments, the A-scans can be obtained by OCT scanning. The systems 100, 200, and/or 300 can be used to acquire the A-scans. Multiple 1-D A-scans can be assembled into a cross-sectional 2-D B-scan. The cross-sectional B-scan image of the retina may be presented on a logarithmic intensity scale as is common for OCT data. Multiple 2-D B-scans can be assembled into a 3-D OCT volume by combining the 2-D B-scans in the C direction. For example, the 3-D OCT volume may include 80 B-scans, each including 150 A-scans.

For the cross-sectional view 400, the operator adjusted the focus to a retinal layer of interest 310 (i.e., the photoreceptor layer) using the variable focus lens with the B-scan images as guidance. In the illustrated embodiment, a thickness t of the layer of interest 310 was about 10 µm, while a thickness T of the entire retinal layer of interest was about 250 µm. In the software tool, the operator may interactively select the retinal layer to focus on, and may activate axial tracking in the software, displaying the en face images that were used for the image quality metric also in real time. For the cross sectional image 400, the subject was instructed to blink and then focus on a fixation target, at which time the aberration correction was initiated using the WSAO algorithm as described below with reference to FIG. 5. The time required to optimize the first 5 modes was about 4 s, after which the subject was permitted to blink and refocus. The operator could either save images after the first optimization, or elect to continue the optimization of the last three modes, which required another about 2 s. During saving, the acquired data was streamed to disk for post processing.

The wavefront aberrations are represented using a set of orthonormal Zernike polynomials (or modes), which permits optimization of each Zernike mode independently. In one embodiment, the method first optimizes for defocus (Z=4), followed by two astigmatisms (Z=3, 5) and then the two comas (Z=7, 8). For each Zernike mode, the optimization is performed by acquiring an OCT volume for 10 different coefficients of each Zernike mode applied to the actuators of wavefront modifying element (e.g., MAL). For each coefficient value, an en face image is extracted, and the coefficient that produced the brightest image is selected as the optimal value. The optimization of the next Zernike mode continues in a hill climbing fashion, using the combination of the previously optimize modes as a starting point. Based on the acquisition parameters of the spectrometer, the optimization can be completed in about 4 s. When imaging human eye, the optimization should be performed within about 4 s. It is desirable for the patient comfort. After about 4 s, the person cannot fixate, and needs to blink. On the other hand, when imaging anesthetized mice, the aberration correction may take longer, on the order of 30 s or a minute.

In some embodiments, the required wavefront correction could be estimated using pupil segmentation, or other approaches well known to practitioner skilled in the art. Pupil segmentation is a method of wavefront sensorless adaptive optics in which the wavefront aberrations are estimated by dividing the input beam into segments along the cross-sectional profile of the beam at a plane that is typically conjugated to the pupil. The lateral shift of the images acquired from a particular beam segment relative to a reference image (i.e., from the central segment) can be used to infer the relative slope of the wavefront at that segment. After measuring the wavefront slope variations across the pupil, they can be assembled by a person of ordinary skill and combined to control the wavefront correcting element to remove or reduce the aberrations.

Figure 5A:
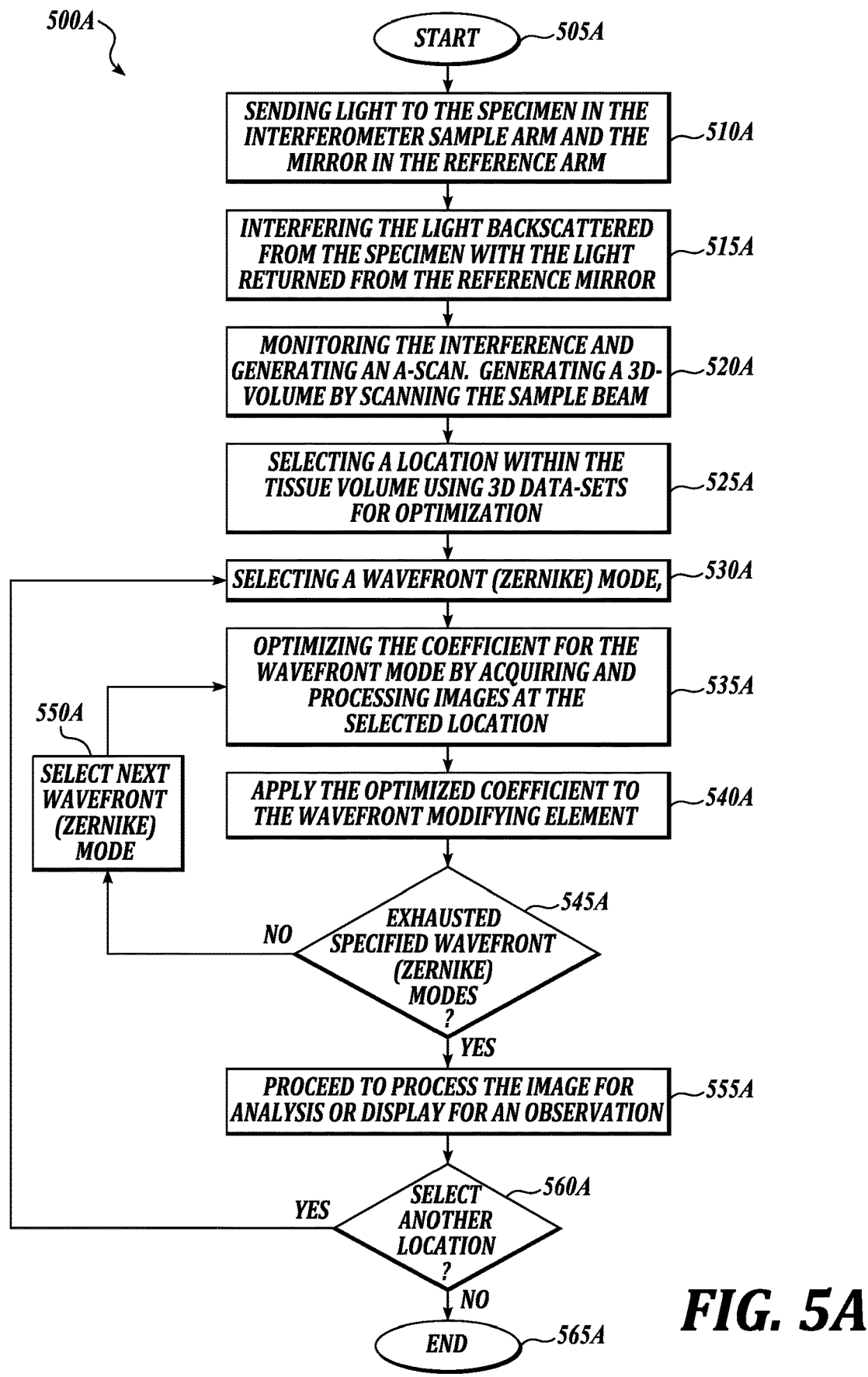
FIGS. 5A and 5B are flow charts of the image acquisition and analysis in accordance with an embodiment of the presently disclosed technology.

FIG. 5A is a flow chart of a high level description of the proposed sensor-less adaptive optics OCT method 500A in accordance with an embodiment of the presently disclosed technology. In some embodiments, some steps illustrated in the method 500A may be omitted, and/or some steps not shown in FIG. 5A may be added.

The illustrated method 500A starts at step 505A. At step 510A, light is sent to the specimen in the optical delivery unit of the interferometer and the mirror in the reference arm (e.g., as described in FIG. 2). At step 515a, the light backscattered from the specimen is interfered with the light returning from the reference mirror at the coupler as shown in, e.g., FIG. 2 or at the beam-splitter as shown in FIG. 1.

At step 520A the interference is monitored using a detector (i.e., an OCT sensor) as shown in, e.g., FIG. 2 or another OCT sensor such as a spectrometer as shown in FIG. 1. The data are processed to generate 1-dimensional OCT A-scans. The beam is scanned across the sample to generate 3-D data-sets.

At step 525A, a location is selected within the tissue volume using 3-D data-sets for optimizing wavefront coefficients of (wavefront modes). In some embodiments, in order to compensate for axial motion during the acquisition, a real time automated retinal tracking software can be used to extract the correct layer within the tissue throughout the optimization process. Next, at step 530A, a wavefront mode (e.g., Zernike term if wavefronts are represented using Zernike polynomials or modes) is selected for optimizing wavefront. At step 535A the wavefront (or Zernike) coefficients are optimized by processing the images at the selected location.

At step 540A, the method applies the optimal coefficient to the appropriate actuator of the wavefront modifying surface.

At step 545A the method checks if all wavefront (or Zernike) modes have been processed. If more modes need to be optimized, the method selects the next mode at step 550A and then repeats steps 535A-545A.

At step 555A, the image is further analyzed (or displayed for an observation). At step 560A, if more wavefronts need to be optimized for the light backscattered from different locations, the method proceeds to step 530A and repeats steps from step 535A onward. Otherwise, in no more wavefronts need to be optimized, the method finishes at step 565A.

Figure 5B:
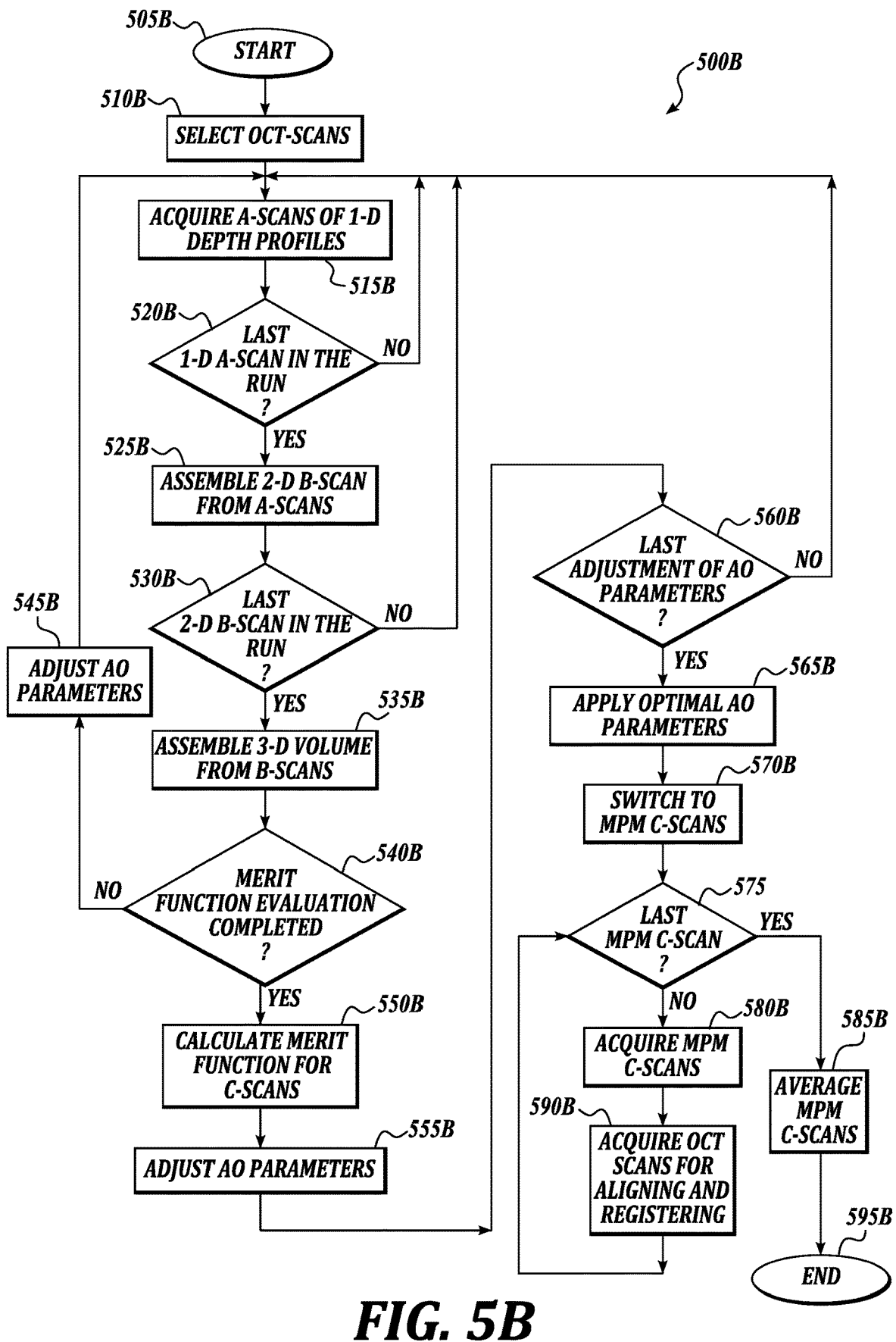

FIG. 5B is a flow chart of an image acquisition and analysis method 500 in accordance with an embodiment of the presently disclosed technology. In some embodiments, some steps illustrated in the method 500B may be omitted, and/or some steps not shown in FIG. 5 may be added.

The illustrated method 500B starts at step 505B. At step 510B, the operator (or the computer) selects the OCT-scans. In some embodiments, the OCT scans may be obtainable using light source including a femtosecond laser or a wavelength-swept laser or a broad-band superluminiscent diode or other broad-band light source. Generally, the OCT-scans use relatively low energy, therefore reducing the stress on the retina of the eye.

At step 515B, 1-D A-scans are obtained. The A-scans may, for example, represent the retina and the surrounding tissue of the eye. At step 520B, a count of the A-scans is taken to verify whether all 1-D A-scans required for a 2-D B-scan have been acquired. If all A-scans have been acquired, the method proceeds to assemble 2-D B-scan from the A-scans at step 525B. Otherwise, the method returns to step 515B.

At step 530B, a count of the B-scans is taken. If all 2-D B-scans required for a 3-D OCT volume have not been assembled yet, the method returns to step 515B. Otherwise, if the required 2-D B-scans have been acquired, the method proceeds to assemble a 3-D OCT volume from 2-D B-scans.

At step 540B, a merit function can be run on the 3-D OCT volume. Some sample merit functions can be light intensity in a given plane of the 3-D OCT volume, contrast, number and sharpness of the boundary lines in the plane, etc. Some other merit functions could also include power in the certain spatial spectral region or some other spatial frequency characteristics. After the merit functions are determined, the optimal merit function can be selected by, for example, comparing the merit functions against those of other images acquired with different values of the Zernike (or wavefront mode) coefficients applied to the actuator(s) of the wavefront correcting element. In some embodiments, the merit function that provides, e.g., the highest image intensity or image sharpness can be selected for the adaptive optics (AO) or wavefront adjustment of step 545B. Furthermore, in some embodiments, image irregularities can be evaluated at step 540B. For example, if the subject blinked or significantly moved the eye, the 3-D OCT volume may become invalid, which would be reflected in the values of the merit functions, and would signify a need to repeat the measurements for the particular 3-D OCT volume starting from, for example, step 515B.

At step 545B, the adaptive optics (AO) parameters are adjusted. For example, wavefront modifying elements 21, 21a, 21b (MAL, VL, VFL) may be adjusted to change/reduce aberrations. In some embodiments, Zernike or wavefront modes can be optimized by adjusting the wavefront modifying elements 21, 21a, 21b. For example, for each Zernike or wavefront mode, the MAL can be stepped through a range of coefficient values. After step 545B, the method returns to step 515B to continue with the acquisition of the A-scans.

After computing the merit function, the method proceeds to step 550B where C-scans can be assembled and their merit functions can be determined. For example, sample C-scans may be generated from the 3-D OCT volume along the retinal layers 310 shown in FIG. 4. At step 550B, a merit function can be determined for the C-scans. For example, an en face image corresponding to the layer of interest can be extracted from the OCT volume to compute the merit function. In some embodiments, the 3-D OCT volume can include just one 2-D B-scan.

At step 555B, the wavefront modifying elements can be adjusted using corresponding actuators. In some embodiments, in order to compensate for axial motion during the acquisition, a real time automated retinal tracking software can be used to extract the correct retinal layer throughout the optimization process. Using a hill climbing algorithm (or other extremum-seeking algorithms), the coefficient that resulted in the brightest image can be identified, applied to the actuators of the MAL, and the next Zernike mode can be searched. For example, wavefront modifying elements 21, 21a, 21b (MAL, VL, VFL) may be adjusted to change, e.g., a focal length of one or more adaptive optics elements. Any other optimization algorithm can be used to obtain optimal coefficients for correcting the wavefronts.

At step 560B, the method verifies whether the adjustments of the wavefront correcting parameters have been completed. If the adjustments have been completed, at step 565 the method can apply the optimal parameters to the wavefront modifying elements. The optimal parameters may be based on the calculated merit functions from step 550B.

In some embodiments, the OCT imaging is combined with multi-photon microscopy (MPM). At step 570B, the system switches to multi-photon microscopy (MPM) C-scans. In general, the MPM scans require higher energy, which, in turn, stresses the retina more than the OCT scans. However, at this step, the adaptive optics elements or wavefront modifying elements (e.g., MAL, VL, VFL) may already be properly adjusted to minimize aberrations, therefore tightly focusing the light source and facilitating relatively quick MPM scan on the order of, for example, 2-5 seconds using relatively lower power of the source.

At step 575B, the method verifies whether the last MPM C-scan has been acquired. If more MPM C-scans are to be acquired, the method proceeds to step 580B to acquire additional C-scans. In some embodiments, in conjunction with acquiring the MPM C-scans at step 580B, the method may also acquire OCT scans at step 590B. These OCT scans may be used to align and register the patient eye to improve the registering of the MPM scans. For example, in at least some embodiments, the MPM scans result in a relatively low signal to noise (S/N) ratio. Therefore, multiple MPM C-scans can be summed up to improve the S/N ratio at least if the noise is random. To properly sum and average the MPM C-scan from step 580B, the corresponding OCT scans from step 590B can help to ascertain correct physical location of the MPM C-scans. The MPM C-scans can be averaged in step 585B. The method may terminate at step 595B.

The inventive technology embodies several advantages over the conventional technologies. Some examples of the advantages are:

1. High energy MPM C-scans are executed after the adaptive optics optimization (e.g., aberration correction, focal depth choice, etc.) had already been performed based on the low energy OCT scans. As a result, the stress on the retina is reduced;

2. Sensor-less adaptive optics design (e.g., Wavefront modifying lenses MAL, VL) results in a smaller system size and system simplification (e.g., no issues with isolating the sensors from the back scattered light);

3. Same optical delivery path (e.g., the optical delivery path 86) is used for both for MPM and OCT scans ("coregistration");

4. Adaptive optics optimization is based on merit function (e.g., contrast, intensity, etc.) and/or application of Zernike function (or other suitable functions) or other suitable wavefront modes;

5. A compact, sensor-less adaptive optics OCT system where wavefront aberrations are estimated using optimization algorithm(s); and 6. The use of OCT for the optimization provides coherence gated depth resolved images, permitting accurate layer-selective aberration correction even in the presence of multi-layered samples.

Several representative applications of the inventive technology are described with reference to FIGS. 6A-8D.

Figure 6A:
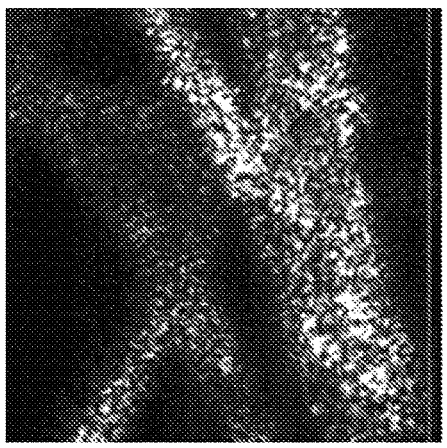
FIGS. 6A-6F are sample images of the structures of an imaging eye phantom acquired in accordance with an embodiment of the presently disclosed technology.
Figure 6B:
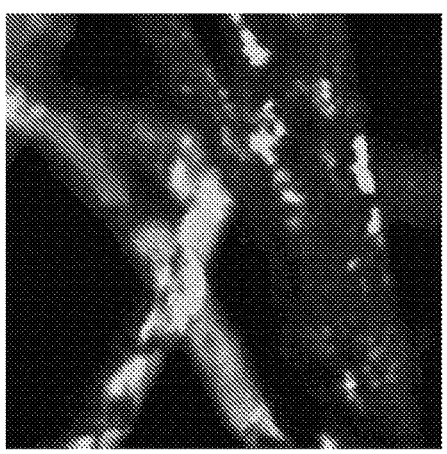
Figure 6C:
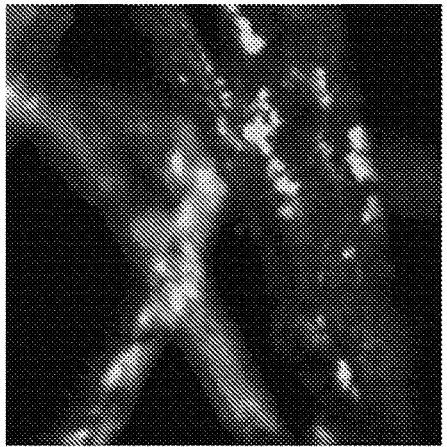
Figure 6D:
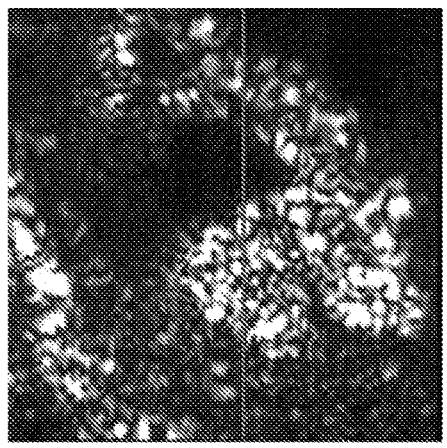
Figure 6E:
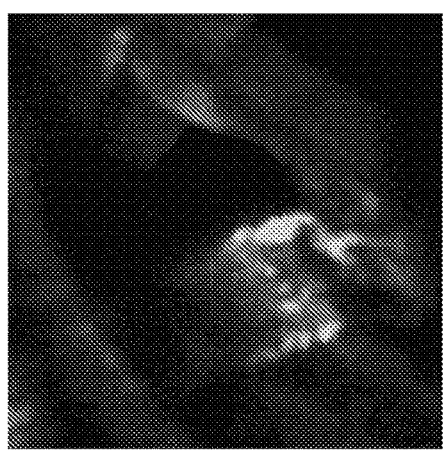
Figure 6F:
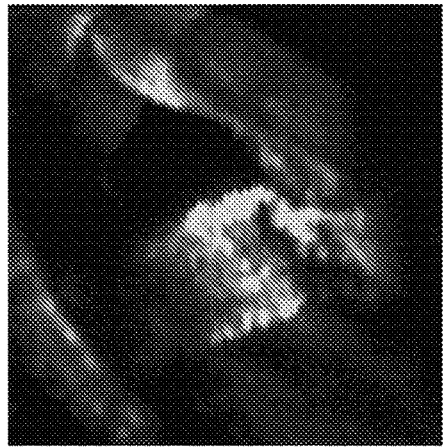

FIGS. 6A-6F are sample images of the structures of the imaging phantom acquired in accordance with an embodiment of the presently disclosed technology. The impact of OCT-image-guided WSAO (e.g., wavefront modifying elements 21, 21a, 21b) wavefront correction on the quality of the MPM images was demonstrated on an imaging phantom. Lens paper stained with a fluorescent dye (excitable by a two photon process at the 780 nm, but not by a single photon at the fundamental wavelength) was covered with a layer of clear epoxy and sealed with a microscope coverslip. The purpose of the epoxy and coverslip was to introduce distortions for the demonstration of aberration correction with the OCT-image-guided WSAO. The fibers in the lens paper provided a structural back-scattering image for the OCT, with the intention of improving the TPEF signal from the dye, which represents the signal of interest in the phantom. Using the OCT data for optimization, TPEF images from the same location are presented before and after aberration correction in FIGS. 6A-6F. In particular, FIGS. 6A and 6D represent OCT en face images. FIGS. 6B and 6E are MPM images (e.g., two-photon excited fluorescence images) without adaptive optics (AO) optimization. FIG. 6B is acquired without AO optimization and FIG. 6C is acquired with optimized coefficients using OCT images corresponding to FIG. 6A. Similarly, FIG. 6E is a MPM image acquired without adaptive optics (AO) optimization and FIG. 6F is a MPM image acquired with AO optimization corresponding to FIG. 6D. The OCT en face image represents the structural appearance of the sample, but is not necessarily of particularly high aesthetic quality due to the large speckle. The purpose of the OCT was to provide depth-resolved aberration correction and cross-sectional aiming of the focal plane in order to improve the MPM; therefore having exquisite structural images was not important for this demonstration. The MPM image (i.e., a two-photon excited fluorescence or TPEF image) acquired after optimization is brighter and contains more detail in comparison to the images acquired before aberration correction. The TPEF images presented are an average of 10-20 frames.

An embodiment of the invention is to use a "woofer-tweeter" configuration if a single wavefront correcting element with large stroke and spatial frequency is not available. In one embodiment, the MAL was used for fine tuning of the focus as well as higher order aberration correction. Although the MAL is capable of correcting aberrations up to $4^{th}$ order Zernike polynomials or modes, we may restrict the aberration correction to those with highest impacts for a 5 mm beam at the pupil, for applications such as human retinal imaging. The modes used were defocus, two astigmatisms, two coma, sphere, and two trefoils, corresponding to Zernike modes 4, 3, 5, 7, 8, 12, 6, 9, respectively. The generalized WSAO optimization algorithm includes, for each Zernike mode, stepping the MAL through a range of coefficient values. At each step, an OCT volume was acquired, and an en face image corresponding to the layer of interest was extracted.

The systems and methods proposed here are not limited to the aberrations described above and are applicable to other wavefront-modifying or correcting elements and other orders of Zernike polynomials (or other orders of wavefront aberration modes).

In order to compensate for axial motion during the acquisition, real time automated retinal tracking algorithm or method or software was used to extract the correct retinal layer throughout the optimization process. The image quality metric was calculated based on the intensity of the en face OCT image, although other parameters, including OCT image sharpness could also be used. Using a hill climbing algorithm, the coefficient that resulted in the brightest image was applied to the MAL, and the next Zernike mode was searched. A person of ordinary skill would know where to look for the details of the hill climbing algorithm (e.g., https://en.wikipedia.org/wiki/Hill_climbing). One could also use other optimization algorithms to find optimal coefficients. In this embodiment, we used 10 steps per mode, however this could be reduced to speed up the optimization time. During optimization, the OCT volume size comprised of 150×80 A-scans, which corresponded to an en face image acquisition and processing rate of 12.5 frames per second. In some scans, en face image was generated by extracting and mapping the intensities from the user-selected depth region within the OCT volume. The brightness of this 2-D en face image was calculated by summing the intensity of each pixel and used as the merit function for the WSAO optimization.

Figure 7A:
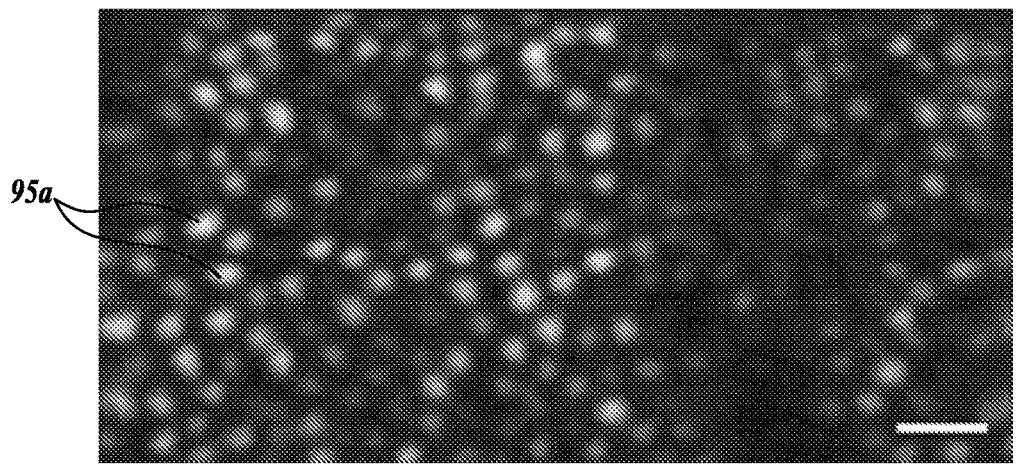
FIGS. 7A-7C are sample images of the retina of the eye acquired in accordance with an embodiment of the presently disclosed technology.
Figure 7B:
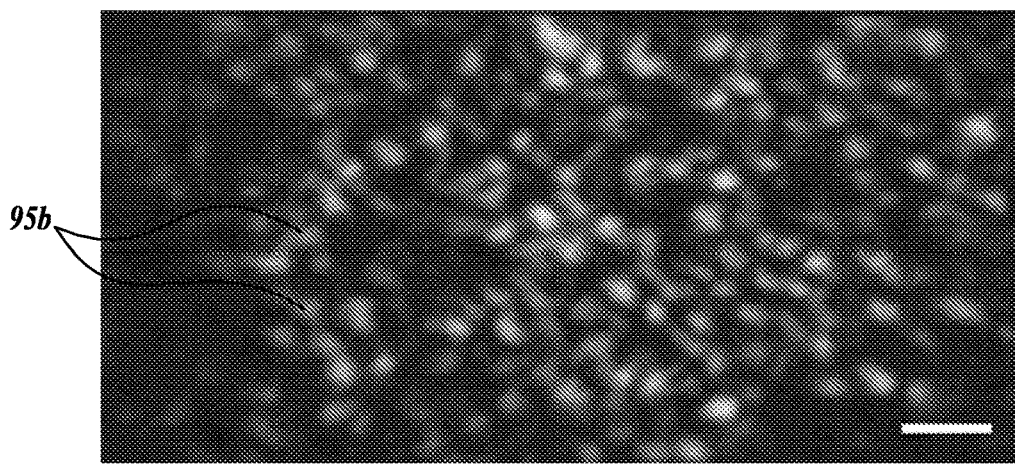
Figure 7C:
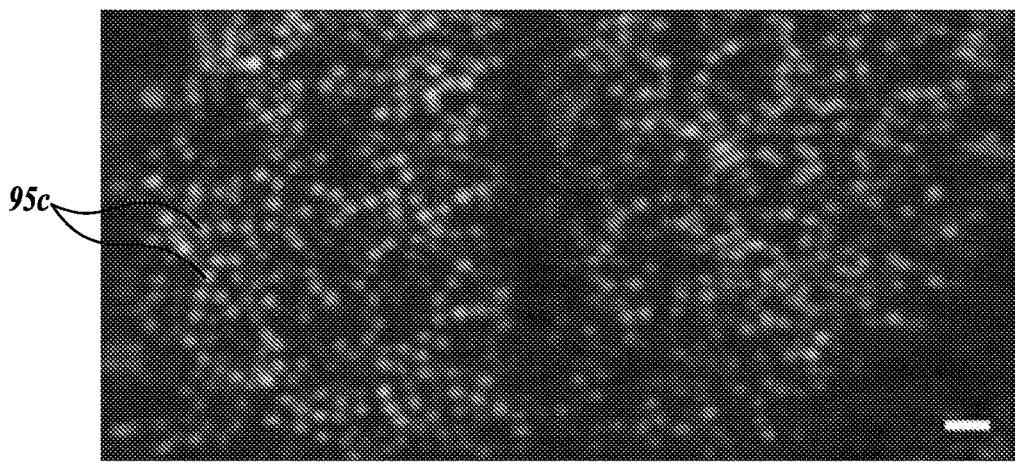

FIGS. 7A-7C are sample images of the retina of the eye acquired in accordance with an embodiment of the presently disclosed technology. The impact of the adaptive optics is demonstrated on en face images with the field of view reduced. Images of human retina were acquired at a retinal eccentricity of about 3°. These images we acquired by first aligning the subject's fovea approximately with the central field of view of the OCT system (in widefield mode), and then instructing the subject to focus on an off axis fixation target. Aberration correction was performed on a small field of view, which was then increased for visualization. The change in appearance of the photoreceptor layer can be observed before and after optimization as brighter and better defined circular photoreceptor structures. FIG. 7A shows an en face image on a small field of view acquired after aberration correction through metric function optimization, and FIG. 7B shows an en face image before optimization. Therefore, spots 95a in FIG. 7A appear brighter and better defined than similarly situated spots 95b in FIG. 7B. The same region is presented in FIG. 7C after optimization with a larger field of view.

Figure 7D:
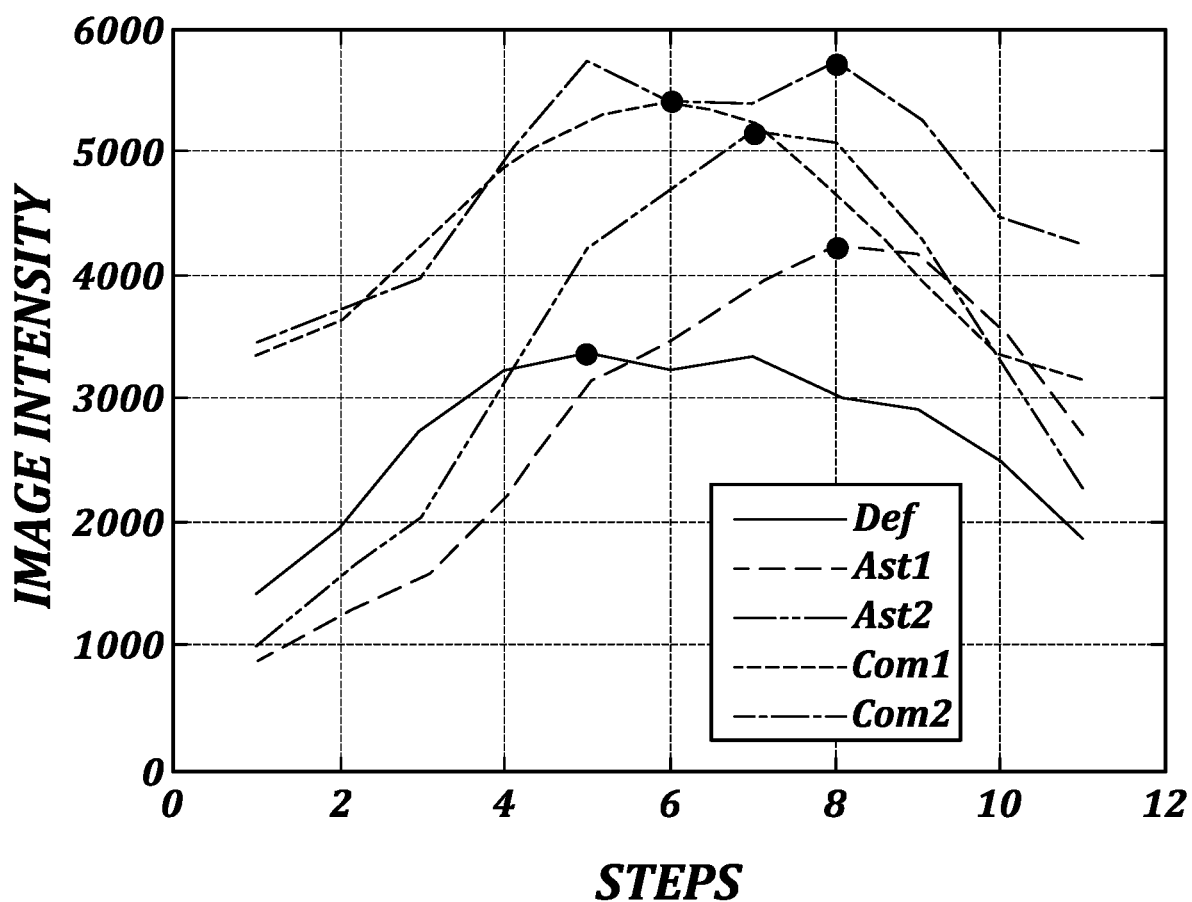
FIG. 7D is a graph of the image intensity versus steps in accordance with an embodiment of the presently disclosed technology.
Figure 8A:
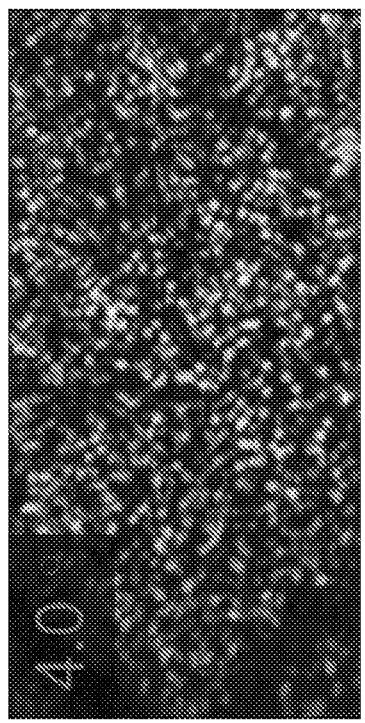
FIGS. 8A-8D are sample images of the retina of the eye acquired in accordance with an embodiment of the presently disclosed technology.
Figure 8B:
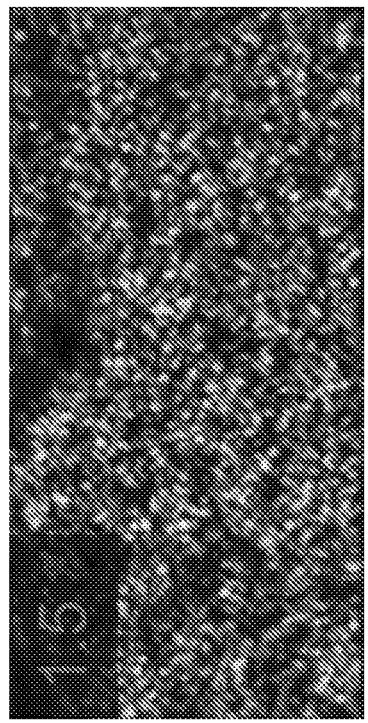
Figure 8C:
Figure 8D:
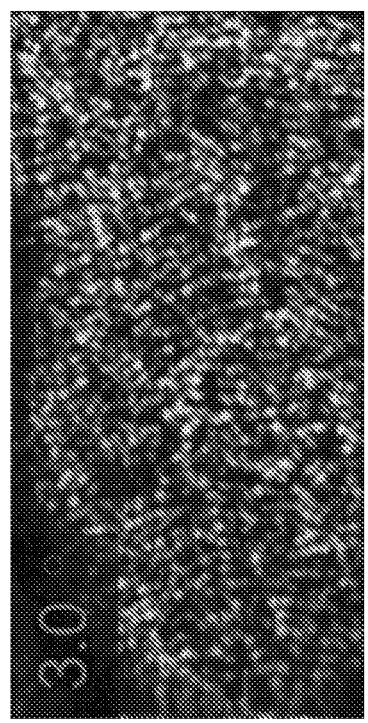

FIG. 7D is a graph of the image intensity versus steps in accordance with an embodiment of the presently disclosed technology. The horizontal axis shows the number of steps undertaken at, for example, step 550B of FIG. 5. The vertical axis shows the results of the merit function. In particular, the image intensity is used, but other merit functions, for example the image contrast, may also be used. The particular aberration modes presented here are defocus (DEF), astigmatism (Ast1 and Ast2), and coma (Com1 and Com2). Black dots for each aberration mode represents a local image intensity maximum for that mode, generally indicating the best achievable aberration correction for a particular mode. The values of the merit function are presented for each mode during the hill climbing optimization, but other optimization schemes are also possible. The 'hill climbing' effect of the algorithm is clearly observed, where the coefficients corresponding to the maximal merit function were selected.

FIGS. 8A-8D are sample images of the retina of the eye acquired in accordance with an embodiment of the presently disclosed technology. A series of photoreceptor images acquired from the same subject at different retinal eccentricities along the horizontal axis from the optic nerve head toward the fovea. At each retinal location, the system was re-optimized in order to acquire the best images possible. The cone photoreceptors at large eccentricity are larger than the closely packed cones near the fovea. The limits of the resolution are visible at the lower eccentricities, where the appearance of the tightly packed cones approaches the resolution of the system.

Generally, the sample results demonstrate that the wavefront-sensorless adaptive optics (WSAO) inventive technology for high resolution imaging can be very flexible for different retinal features. In addition to aberration correction on the outer retina (photoreceptor mosaic), the technology can also correct aberrations on structures of the optic nerve head. Since the image information is used for aberration correction, the anatomical features on which the image-based optimization is performed is generally known, although the method can be applied on the anatomical features that are not known a-priori.

Many embodiments of the technology described below may take the form of computer- or controller-executable instructions, including routines executed by a programmable computer or controller. Those skilled in the art will appreciate that the technology can be practiced on computer/controller systems other than those shown and described below. The technology can be embodied in a special-purpose computer, controller or data processor that is specifically programmed, configured or constructed to perform one or more of the computer-executable instructions described below. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like). Information handled by these computers can be presented by any suitable display medium, including a CRT display or LCD.

The technology can also be practiced in distributed environments, where tasks or modules are performed by remote processing devices that are linked through a communications network. In a distributed computing environment, program modules or subroutines may be located in local and remote memory storage devices. Aspects of the technology described below may be stored or distributed on computer-readable media, including magnetic or optically readable or removable computer disks, as well as distributed electronically over networks. Data structures and transmissions of data particular to aspects of the technology are also encompassed within the scope of the embodiments of the technology.

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

The embodiments of the invention in which an exclusive property or privilege is claimed are defined as follows:

1. A sensorless adaptive optics imaging system, comprising:
   a source of light;
   an optical delivery unit having at least one wavefront modifying element;
   an optical coherence tomography (OCT) sensor configured to acquire OCT images based on a light emitted by the source of light and transmitted through the optical delivery unit, wherein the OCT images are 3-D OCT volume images that comprise 2-D B-scan images, and wherein the 2-D B-scan images comprise 1-D A-scan images;
   a processing unit configured to:
     process the OCT images, and
     determine an adjustment of at least one parameter of the at least one wavefront modifying element; and
   a multi-photon microscopy (MPM) sensor configured to acquire MPM images based on the light emitted by the source of light and transmitted through the optical delivery unit,
   wherein the processing unit is further configured to process the MPM images, and
   wherein the MPM images are 2-D C-scans based on en face images generated by extracting and mapping intensities from user-selected depth regions within the 3-D MPM volume images.

2. The system of claim 1, wherein the acquisition of the 1-D A-scans is synchronized to acquisition of the MPM images by the MPM sensor.

3. The system of claim 1, further comprising a dichroic mirror (DcM) in the optical delivery unit, wherein the DcM is configured to split the light such that an MPM signal goes to one sensor and an OCT signal goes to a different sensor.

4. The system of claim 1, wherein the wavefront modifying element is transmissive and is located adjacent to an objective lens defining a pupil.

5. The system of claim 1, wherein an axial motion of a target is compensated using tracking during acquisition.

6. The system of claim 1, wherein the adjustment of the parameters of the wavefront modifying element is based on at least one of the following modes: Zernike modes, Lukosz polynomials, and natural modes of the wavefront modifying element.

7. The system of claim 1, wherein the wavefront modifying element is selected from a group consisting of a spatial light modulator, a deformable mirror, a liquid crystal, a deformable multi-actuator adaptive lens, a transmissive deformable multi-actuator adaptive lens, a variable focus lens, a deformable variable focus lens and a digital micromirror display.

8. The system of claim 7, wherein one wavefront modifying element is a woofer, and the other wavefront modifying element is a tweeter.

9. The system of claim 1, wherein different light sources are used for the MPM images and the OCT images.

10. The system of claim 9, wherein a wavefront correction is performed with an OCT light source ON and an MPM light source OFF.

11. A method for acquiring images using sensorless adaptive optics, comprising:
    sending light through an optical delivery unit to a target, the optical delivery unit having at least one wavefront modifying element;
    acquiring OCT A-scans of a target by an OCT sensor;
    assembling the OCT A-scan images into 2-D OCT B-scan images;
    assembling the OCT B-scan images into 3-D OCT volume;
    selecting at least one OCT 2-D C-scan image within the 3-D OCT volume;
    determining merit functions of the OCT 2-D C-scan image; and
    adjusting the wavefront modifying element.

12. The method of claim 11, wherein the wavefront is represented by at least one of Zernike modes, Lukosz polynomials, and natural modes of the wavefront modifying element, and wherein coefficients of these modes are selected based on the merit functions of the OCT 2-D C-scan images.

13. The method of claim 12, wherein the merit functions are processed using a hill climbing algorithm to obtain optimal coefficients of Zernike modes.

14. The method of claim 11, further comprising:
    acquiring multi-photon microscopy (MPM) 2-D C-scan images;
    averaging MPM 2-D C-scan images; and
    co-registering the OCT images and the MPM images.

15. The method of claim 14, wherein the OCT 1-D A-scans are acquired by a high speed detector and the MPM 2-D C-scan images are acquired by a photo-multiplier tube (MPM) detector.

16. The method of claim 14, wherein the MPM 2-D C-scan images require a different energy of light than an energy of light for the OCT 2-D C-scan images.

17. The method of claim 11, wherein the wavefront modifying element is selected from a group consisting of a spatial light modulator, a deformable mirror, a liquid crystal, a deformable multi-actuator adaptive lens, a transmissive deformable multi-actuator adaptive lens, a variable focus lens, a deformable variable focus lens and a digital micromirror display.

18. A non-transitory computer-readable medium whose contents cause a computer to acquire and process images using sensorless adaptive optics, the images being acquired and processed by a method comprising:
    sending light through an optical delivery unit to a target, the optical delivery unit comprising at least one wavefront modifying element;
    acquiring OCT A-scans of 1-D depth profile of a target by an OCT sensor;
    assembling the OCT A-scans into 2-D OCT B-scan images;
    assembling the OCT B-scan images into 3-D OCT volume;
    selecting at least one OCT 2-D C-scan image within the 3-D OCT volume;
    determining merit functions of the OCT 2-D C-scan image; and
    adjusting the wavefront modifying element based on merit functions.

19. A sensorless adaptive optics imaging system, comprising:
    a source of light;
    an optical delivery unit having at least one wavefront modifying element;

an optical coherence tomography (OCT) sensor configured to acquire OCT images based on a light emitted by the source of light and transmitted through the optical delivery unit;
a processing unit configured to:
  process the OCT images, and
  determine an adjustment of at least one parameter of the at least one wavefront modifying element; and
a multi-photon microscopy (MPM) sensor configured to acquire MPM images based on the light emitted by the source of light and transmitted through the optical delivery unit,
wherein the processing unit is further configured to process the MPM images,
wherein different light sources are used for the MPM images and the OCT images, and
wherein a wavefront correction is performed with an OCT light source ON and a MPM light source OFF.

* * * * *